(12) United States Patent
Labriola et al.

(10) Patent No.: US 8,338,619 B2
(45) Date of Patent: Dec. 25, 2012

(54) CRYSTALLINE FORM OF THE ZOLEDRONIC ACID, A PROCESS TO OBTAIN IT AND THE PHARMACEUTICAL COMPOSITION COMPRISING IT

(75) Inventors: Rafael Alberto Labriola, Beunos Aires (AR); Dora Graciela Tombari, Buenos Aires (AR); Adriana Vechhioli, Buenos Aires (AR)

(73) Assignee: Gador S.A., Buenos Aires (AR)

( * ) Notice: Subject to any disclaimer, the term of this patent is extended or adjusted under 35 U.S.C. 154(b) by 443 days.

(21) Appl. No.: 12/700,067

(22) Filed: Feb. 4, 2010

(65) Prior Publication Data

US 2010/0197935 A1 Aug. 5, 2010

Related U.S. Application Data

(60) Division of application No. 11/837,277, filed on Aug. 10, 2007, now abandoned, which is a continuation-in-part of application No. PCT/EP2006/004473, filed on May 12, 2006.

(30) Foreign Application Priority Data

Jul. 28, 2005 (AR) ............................ P20050103131

(51) Int. Cl.
*C07D 233/54* (2006.01)
*C07D 233/60* (2006.01)

(52) U.S. Cl. .................................................. 548/341.1

(58) Field of Classification Search ................ 548/341.1
See application file for complete search history.

(56) References Cited

U.S. PATENT DOCUMENTS 4,939,130 A * 7/1990 Jaeggi et al. .................... 514/94

\* cited by examiner

*Primary Examiner* — Rebecca Anderson
(74) *Attorney, Agent, or Firm* — Patent Central LLC; Stephan A. Pendorf

(57) ABSTRACT

A method to obtain a new crystalline form of the Zoledronic acid, characterized by its X-rays diffractogram as well as by its spatial atomic distribution in the red crystalline and its curves of thermal analysis. There is also included a method to obtain this crystalline form, which includes the synthesis of the corresponding acid and the pharmaceutical composition this crystalline form comprises.

27 Claims, 13 Drawing Sheets

Zoledronic Acid trihydrate - Diffractogram of dust X-Rays

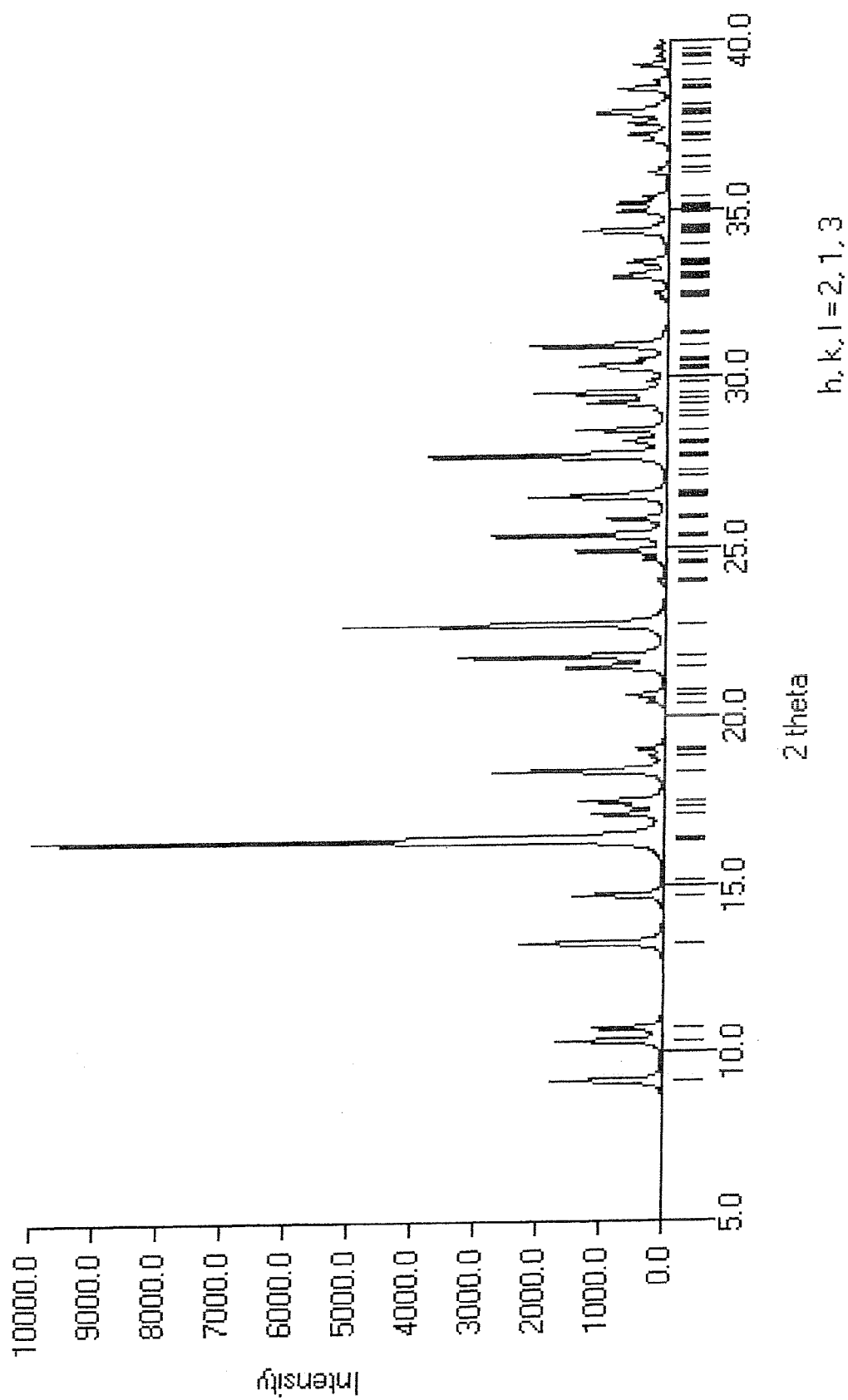

Zoledronic Acid monohydrate - Diffractogram of dust X-Rays

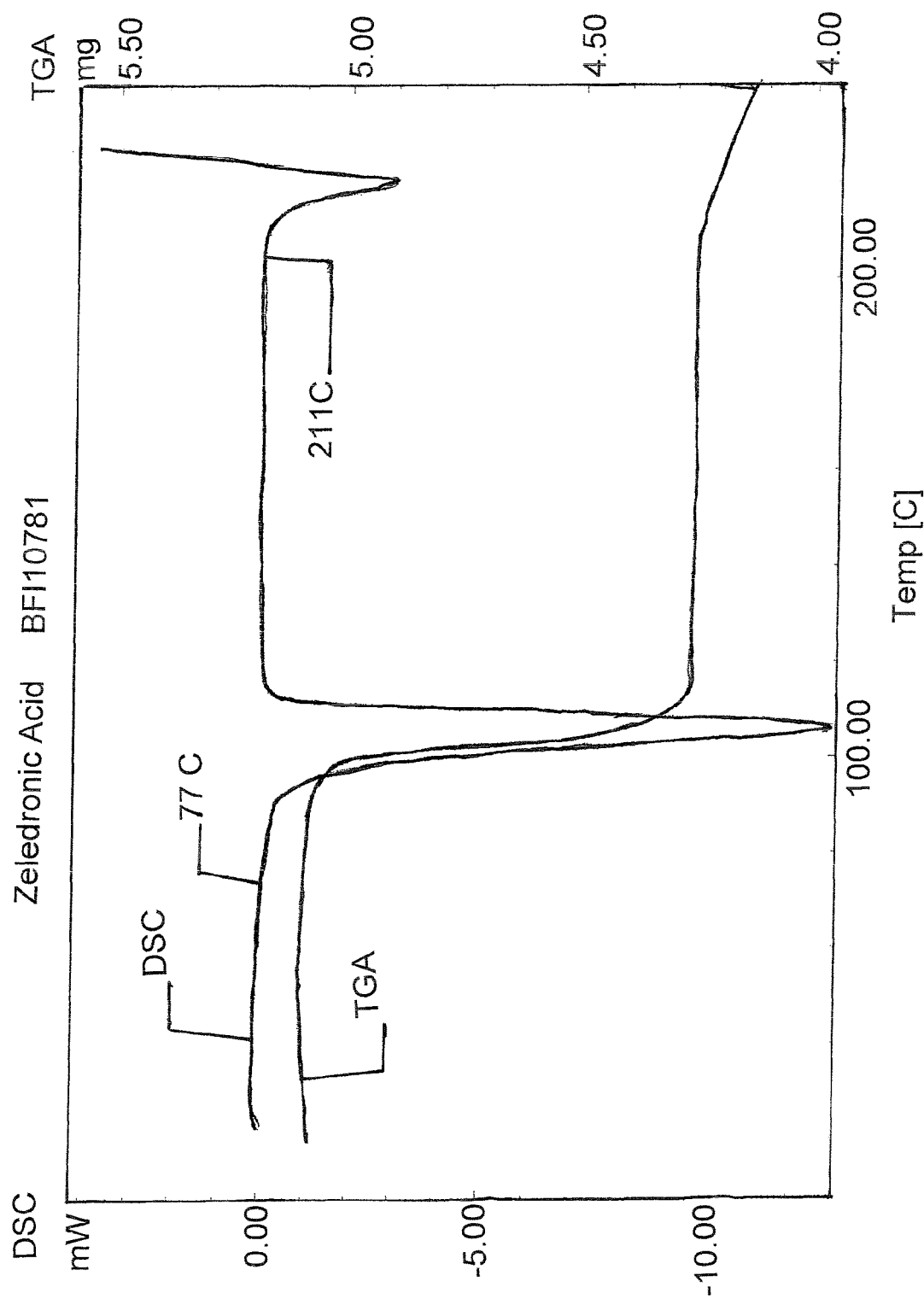
Fig. 2 - Zoledronic acid trihydrate- TGA and DSC

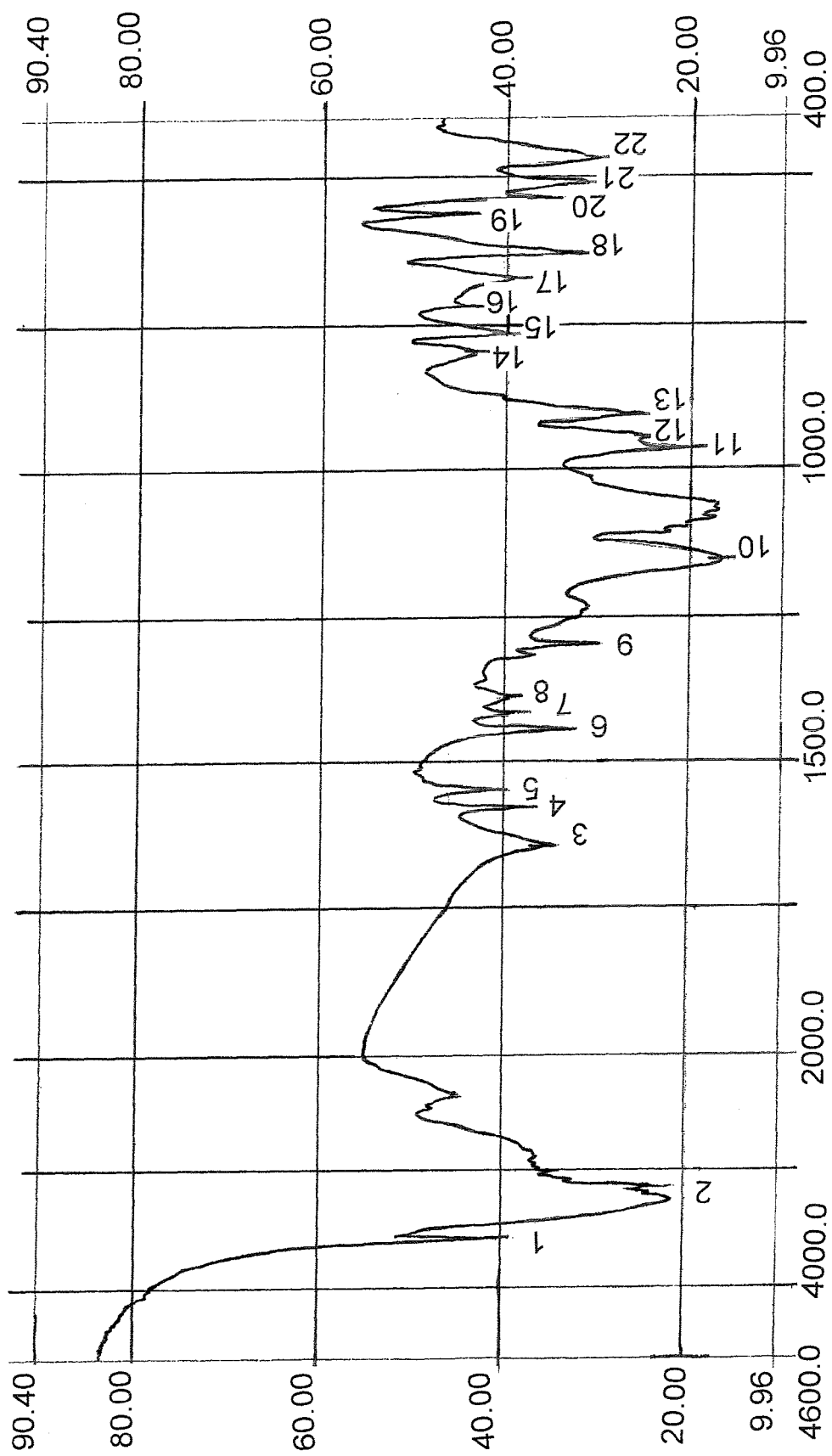
Fig. 3 - Zoledronic acid trihydrate- Infrared Spectrum

Fig. 3 cont. Report picks – Table

| NO. | ABSCISSA | PEAK | HEIGHT |
|---|---|---|---|
| 1 | 3580.4 | 40.02 | 14.58 |
| 2 | 3142.5 | 22.52 | 5.84 |
| 3 | 1643.6 | 35.49 | 8.24 |
| 4 | 1579.9 | 37.99 | 8.05 |
| 5 | 1549.1 | 40.83 | 7.35 |
| 6 | 1443.0 | 33.79 | 10.79 |
| 7 | 1414.0 | 38.83 | 3.94 |
| 8 | 1387.0 | 39.62 | 3.16 |
| 9 | 1294.4 | 30.86 | 7.22 |
| 10 | 1155.5 | 16.67 | 15.18 |
| 11 | 966.5 | 20.16 | 8.62 |
| 12 | 945.3 | 24.84 | 3.74 |
| 13 | 908.6 | 25.73 | 12.17 |
| 14 | 796.7 | 43.27 | 6.55 |
| 15 | 762.0 | 39.99 | 10.23 |
| 16 | 717.6 | 43.86 | 3.59 |
| 17 | 671.3 | 39.31 | 9.47 |
| 18 | 628.9 | 31.97 | 20.20 |
| 19 | 563.3 | 43.82 | 11.53 |
| 20 | 534.4 | 35.22 | 10.02 |
| 21 | 511.2 | 31.82 | 8.97 |
| 22 | 466.8 | 30.16 | 13.15 |

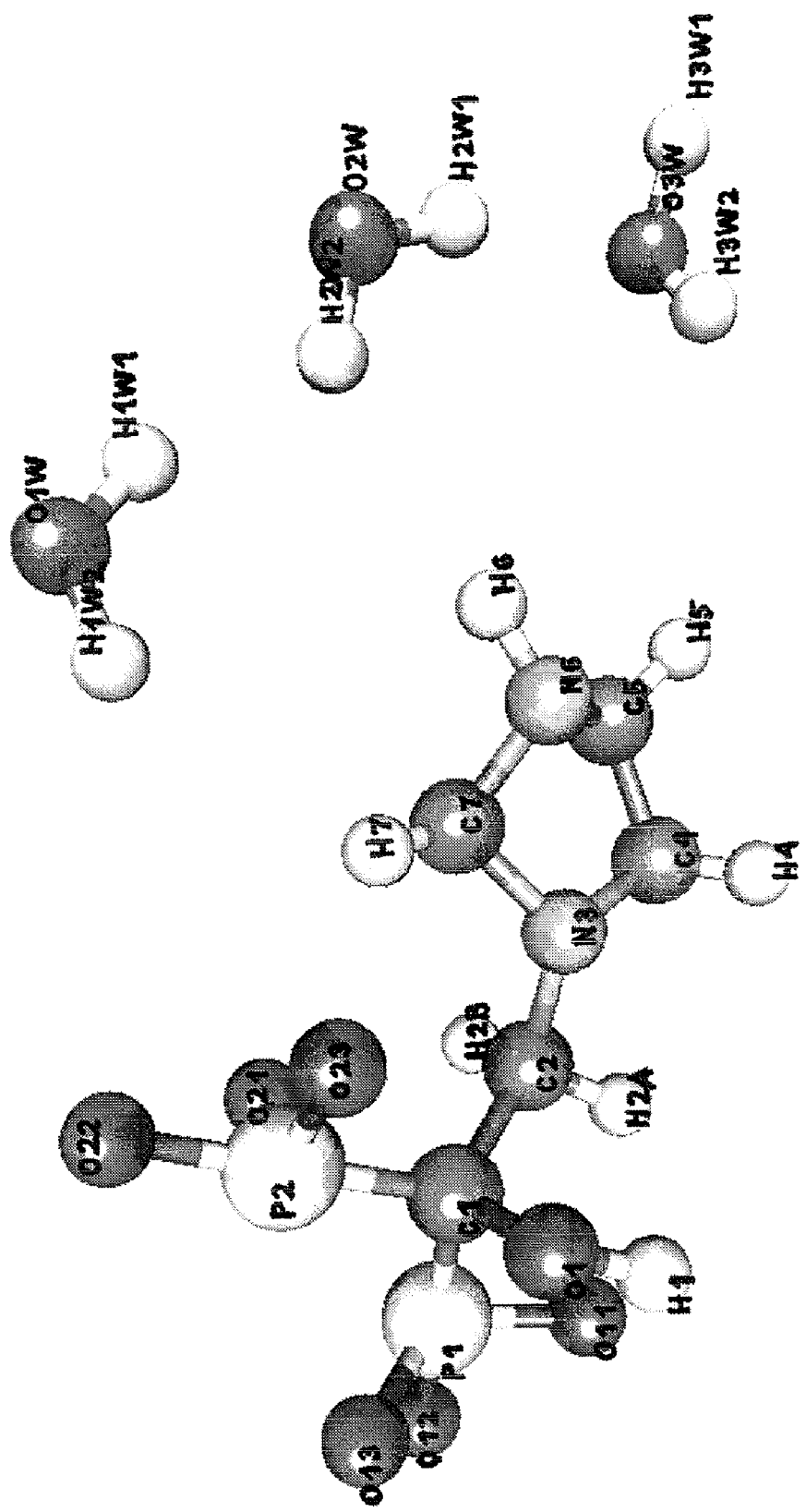
Fig. 4 – Zoledronic acid trihydrate – Spatial layout in the unitary cell

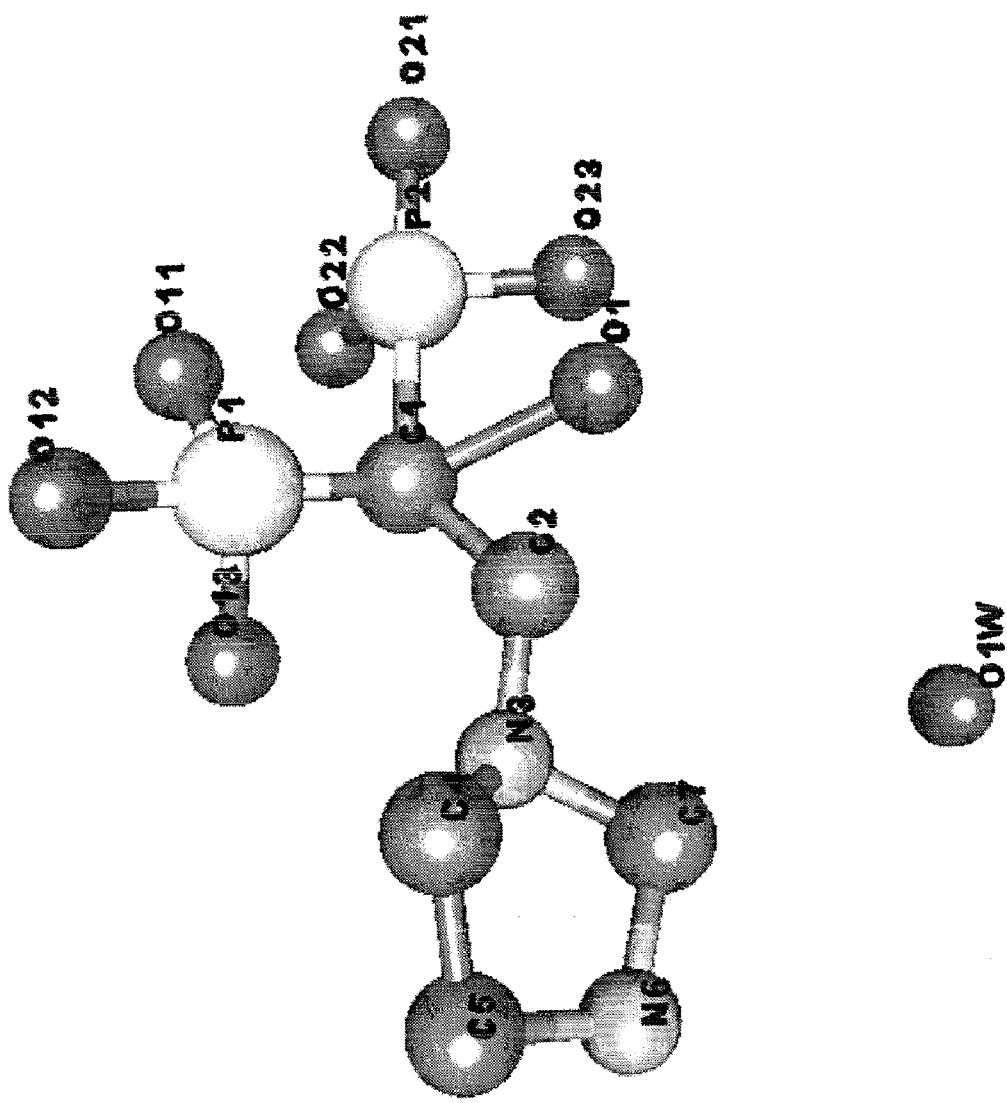
Fig. 4A – Zoledronic acid monohydrate – Spatial layout in the unitary cell

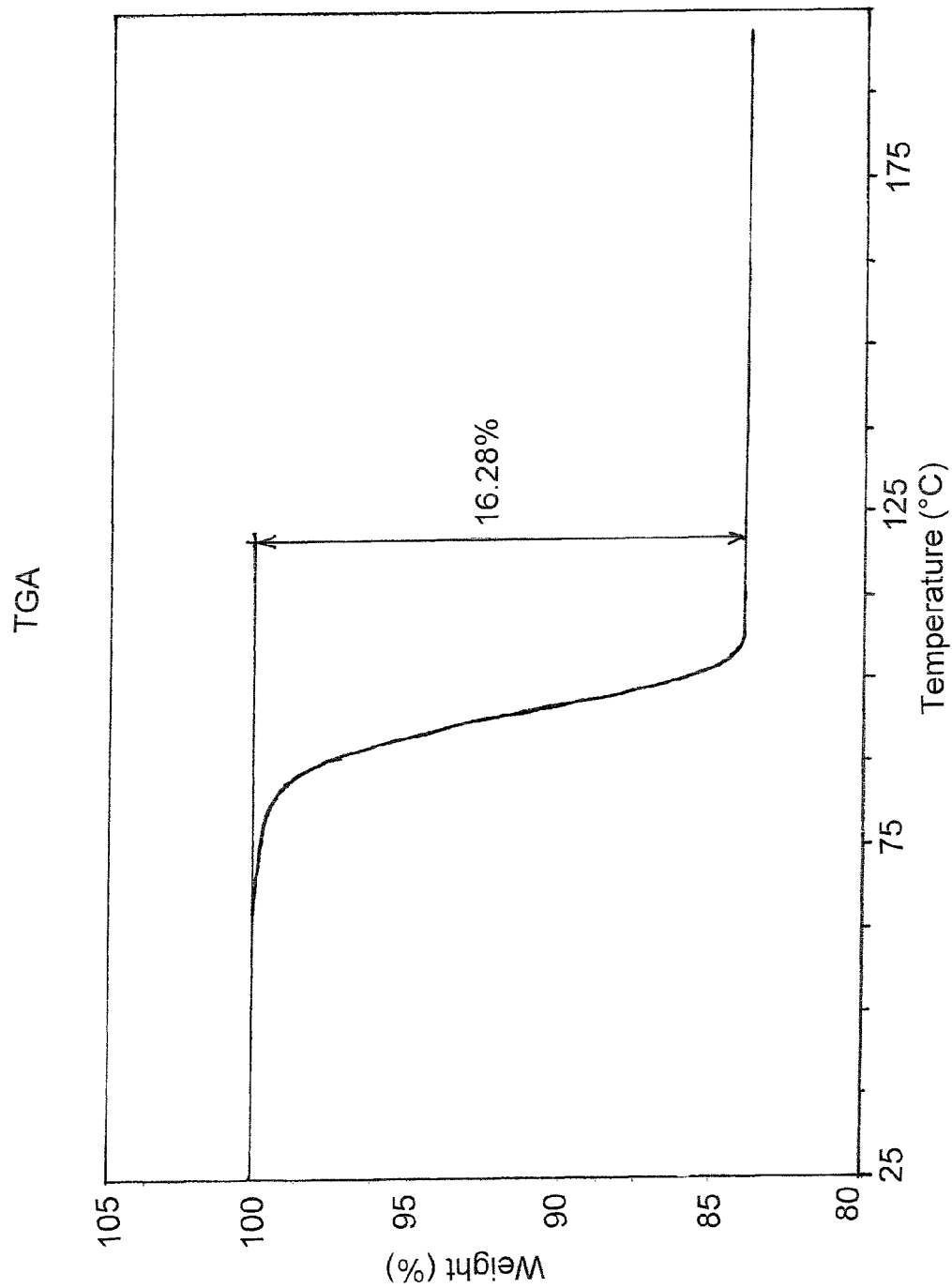
Fig. 5 A  TGA

TGA $$\Delta U = (E_a^f - E_a^b)$$

Where: ΔU= energy difference
  f = reagent
  b = product

TGA

TGA

US 8,338,619 B2

CRYSTALLINE FORM OF THE ZOLEDRONIC ACID, A PROCESS TO OBTAIN IT AND THE PHARMACEUTICAL COMPOSITION COMPRISING IT

FIELD OF THE INVENTION

This invention refers to a new crystalline form of zoledronic acid, characterized by its diffractogram of X-rays as well as by its spatial atomic distribution in the crystalline network and its thermal analysis curves.

There is also included a method to obtain this crystalline form, which comprises the synthesis of the corresponding acid and the pharmaceutical composition comprised by this crystalline form.

BACKGROUND OF THE INVENTION

Zoledronic acid (I) is a bisphosphonic acid, which acts as an inhibitor of bone osteoclastic resorption. This compound, chemically called 1-hydroxy-2-(1-imidazoyl)ethydilene bisphosphonic acid, is sold in the USA under the trade name of Zometa® (zoledronic acid for injectables).

Zoledronic acid belongs to the family of the bisphosphonates well known for its features useful when treating diseases caused by dysfunctions in the metabolism of calcium and phosphorous [see for example K. R. Williams-J. C'hem. Ed. 81, 1406 (2004)].

There exist several patents describing methods for the obtention of bisphosphonates, particularly for zoledronic acid and its salts. DE 3626058 (1988); U.S. Pat. No. 4,777,163 (1988); EP 258618 (1988); U.S. Pat. No. 4,939,130 (1990) could be mentioned.

In Chemical Abstract Services, there are various forms of free zoledronic acid and its salts registered:

1. Anhydrous Zoledronic acid (RN: 118072-93-8).
2. Monohydrate Zoledronic acid (RN:165800-06-6).
3. Zoledronic Acid, anhydrous disodium salt (RN: 131654-46-1).
4. Zoledronic Acid, monohydrate disodium salt (RN: 165800-07-7)
5. Zoledronic Acid, monohydrate trisodium salt (RN: 165800-08-8).
6. Zoledronic Acid, magnesium salt (RN: 157432-59-2).
7. Zoledronic Acid, zinc salt (RN:157432-58-I).

U.S. Pat. No. 4,939,130 describes that the zoledronic acid obtained has a melting point of 239° C.

Particularly, in the request of patent US Serial No. 2005/0054616 diverse crystalline forms are described for the free acid and its sodium salts.

Seven crystalline forms of zoledronic acid are described in this document, identified as forms I, II, XII, XV, XVIII, XX and XXVI through their diffractograms of X-rays and TGA (Thermogravimetric Analysis).

The use of methansulphonic acid as a solvent in the preparation of alendronic acid and its salts is described in U.S. Pat. No. 4,922,007 (1990) and EP 462663 (1991).

SUMMARY OF THE INVENTION

This invention refers to a new polymorphic form of zoledronic acid which exists in the form of a trihydrate, and to its method of obtaining it.

The existence of a new crystalline stable form and of a simple and reproducible method for obtaining it widens the spectrum of possibilities for the design of new pharmaceutical forms.

The use of the methansulfonic acid as a solvent to prepare zoledronic acid results in a homogeneous reaction.

In other preparations where a diluent is used [see for instance U.S. Pat. No. 4,777,163 (1988) Example 1; US 2005/0054616 (2005) Examples 1-8], the reaction occurs in a heterogeneous phase.

The use of the said methansulphonic acid for obtaining zoledronic acid is described in the literature [G. R. Kieczykowski et al.-J. Org. Chem. 60, 8310 (1995)], nevertheless the yield obtained in that publication, being of 31%, discourages its use at an industrial scale and has not been protected by patents.

In the present case, the use of water as a reactant, the absence of adding phosphorous acid and the molar ratios of reactants and of solvent used, result in significant differences as regards the described procedure giving rise to a substantial increase in the yield up to a value of 83% which turns this process economically apt for the manufacture of zoledronic acid.

Further, the invention is based on the discovery that trihydrate formation is ruled by crystallization temperature, such that trihydrate is obtained when dissolved zoledronic acid is crystallized at a temperature between 5 and 35° C., preferably between 15 and 25° C.

BRIEF DESCRIPTION OF THE DRAWINGS

The invention will now be described in greater detail with reference to the figures, wherein

FIG. 1A is a diffractogram of trihydrate theoretical dust X-rays;

FIG. 1B shows the X-ray powder diffractoaram of monohydrate crystalline form,

FIG. 2 curves obtained through the TGA analysis (Thermogravimetric Analysis) and DSC (Differential Scanning Calorimetry) of this new crystalline form;

FIG. 3 corresponds to the infrared spectrum of this new crystalline form;

FIG. 4 corresponds to the spatial disposition of the atoms in the unit cell of this new crystalline form;

DETAILED DESCRIPTION OF THE INVENTION

The X-ray diffraction analysis and the thermal analysis (TGA, DSC) were carried out at the Atomic Energy National Commission-Condensed Matter Group.

The equipment used is a Philips model X'Pert with a PW3710 unit to obtain the diffractograms of the samples.

A K-Alpha wavelength of 1.54060 Å was used.

The water losses were determined through the TGA (Thermogravimetric Analysis) with a Shimadzu DTG-50 equipment with a 40 ml/mm dry air flow.

The melting points result from the curves obtained through DSC (Differential Scanning Calorimetry) in a Shimadzu DSC-60 equipment at 10° C./min with a 30 ml/min nitrogen flow.

The infrared spectra were carried out in a Shimadzu FTIR-8 100 equipment, using a solid substance in the form of pills with KBr.

The new crystalline form corresponds to a trihydrate, its study by means of X rays of a single crystal shows that the distribution of its atoms in the crystalline network corresponds to the special group P-1, characterized by the following cell parameters (Å): a:6.874; b 9.450; c:10.825; α (alpha): 65.140; β (beta):76.83 0; γ (gamma): 81.390.

Figure 1:
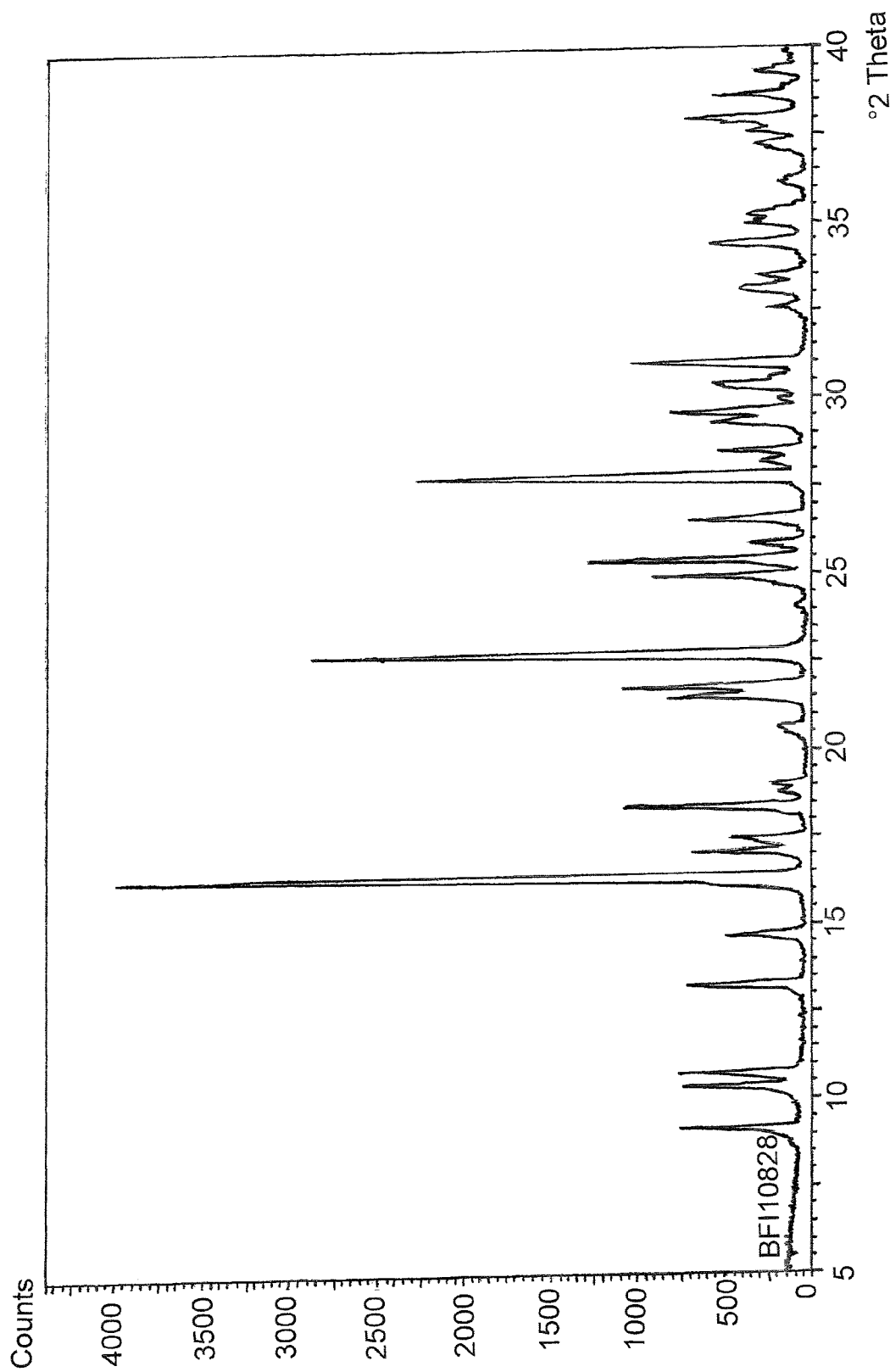
FIG. 1 shows the X-ray powder diffractogram of this new trihydrate crystalline form.
Figure 1:
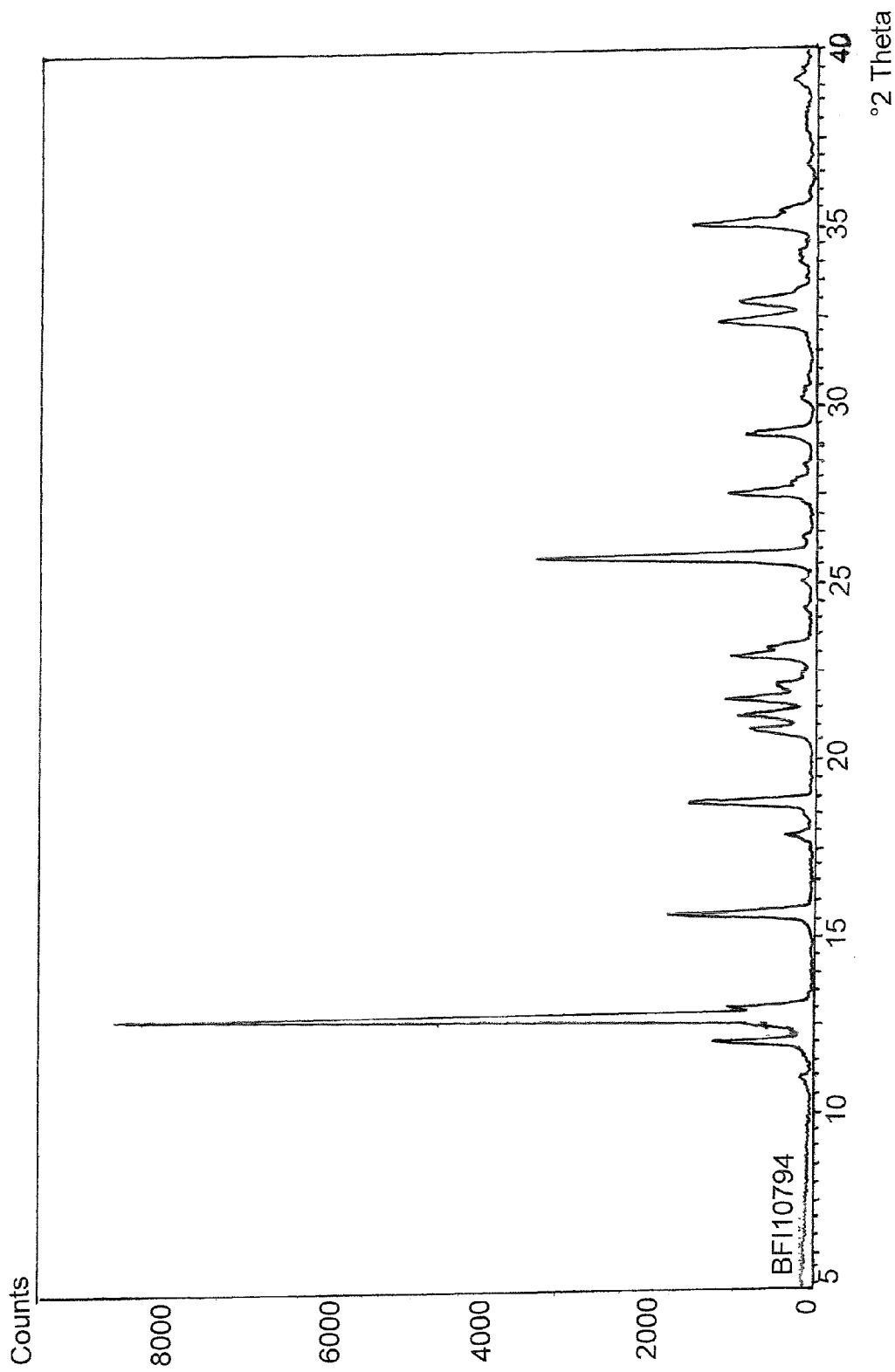

FIG. 1 shows the X-rays powder diffractogram (XRPD) of this new crystalline form.

FIG. 2 corresponds to the curves obtained through the TGA analysis (Thermogravimetric Analysis) and DSC (Differential Scanning Calorimetry) of this new crystalline form.

FIG. 3 corresponds to the infrared spectrum of this new crystalline form.

FIG. 4 corresponds to the spatial disposition of the atoms in the unit cell of this new crystalline form.

The existence of three water molecules for each one of zoledronic acid could be clearly seen in this figure.

In order to compare, the theoretical X-ray diffractogram for the trihydrate form (FIG. 1A), the powder X-rays diffractogram obtained with the form I (monohydrate) (FIG. 1B) and the atoms spatial distribution in the unit cell of the crystalline network for the monohydrate form (FIG. 4A) are also shown.

The trihydrate crystalline form described in this document, by means of the exposure in an environment with 75 to 96% relative humidity at 30-40° C. during 24 hours, does not absorb water and maintains its X-rays powder diffractogram and its thermal profile (TGA and DSC) unchanged.

This new crystalline form of this invention is characterized for presenting in its X ray powder diffractogram peaks in angles of 2θ of 9.2; 10.4; 10.8; 14.7; 16.4; 17.1; 18.4; 21.5; 21.8; 22.8; 25.0; 25.4; 27.8°±0.2°.

Although the XRDP is the best analytical tool, it should not be used alone in the identification and characterization of the solid phases. Some drugs have the same diffractogram (lines) under different solid phases. For the characterization of solid phases, it is always suggested the use of at least three or four analytical tools, i.e.: IR, TG, DSC together with the XRDP.

Accordingly, the product is also characterized because its thermal analysis (TGA and DSC) show an endotherm between 68-128° C. associated to a loss of mass of around 16-17%, which corresponds to a trihydrate and a melting endotherm followed by decomposition at around 211-215° C.

This new trihydrate form has always been obtained in our laboratory without difficulties and in a reproducible way.

Zoledronic acid was prepared by a method not described for this substance and advantageous because of the yield and the quality of the obtained crude product.

The same consists of reacting 1-imidazol-1-yl acetic acid with phosphorous trichloride and water, in the presence of methanesulphonic acid.

The suspension is heated at 60-65° C. over 10-15 hours, preferably between 9-12 hours, whereupon it turns into a viscous solution.

Throughout the reaction, there is significant release of hydrogen chloride.

Once the mass is dissolved by additional addition of water at 8-12° C., it is heated at reflux at 105-112° C. over 3-5 hours.

It is then partially neutralized with aqueous solution of sodium hydroxide up to a pH between 0 and 0.9, preferably between 0 and 0.4 at a temperature between 20 and 40° C. and the crystallization starts.

It is then cooled down to 0-5° C., filtered, washed by resuspension first in water and then in methanol.

The crude zoledronic acid may be obtained by means of drying at 50-80° C. with a yield exceeding 80% and a quality apt for the obtention of the crystalline trihydrate form.

To obtain the crystalline trihydrate form of this invention an aqueous hot solution of zoledronic acid, which concentration varies between 1.5 and 10% (w/v), preferably between 2 and 4% (w/v), is crystallized at a temperature between 5 and 35° C., preferably between 15 and 25° C.

In order to achieve this without the need of using large dilutions, the hot solution is poured over a small amount of water, kept at the wanted crystallization temperature.

In this way, the crystallization temperature is adjusted regulating the volume of the hot solution added and the flow of the refrigerating liquid.

While adding hot solution to refrigerated water is an economical and easy technique for controlling crystallization temperature, other techniques could also be employed, such as, e.g., spraying into chilled air, dripping or onto a chilled metal or glass plate, or running the solution through a chilled metal or glass tube or micropipette, or even pouring over ice rather than liquid water (in every case controlling process parameters such that substantially all crystallization takes place within 5-35° C., preferably between 15 and 25° C.).

Preliminary tests indicate that other solvents are less suitable to obtain trihydrate. For example, when a trihydrate is in contact with methanol it loses water and changes first to monohydrate and then to anhydrous form.

In this way the new crystalline trihydrate form is obtained, whose X-ray powder diffractogram presents peaks in values of 2θ of 9.2; 10.4; 10.8; 14.7; 16.4; 17.1; 18.4; 21.5; 21.8; 22.8; 25.0; 25.4; 27.8°±0.2°. and whose diffractogram corresponds to the one of FIG. 1.

This substance presents the following physicochemical characteristics.

The curve corresponding to the TGA (Thermogravimetric Analysis) is shown in FIG. 2, in which a loss of mass is seen, corresponding to a loss of water, of 16-17%, which corresponds to a trihydrate.

The curve corresponding to the analysis by DSC (Differential Scanning Calorimetry), observed in FIG. 3, shows an endotherm at 211-215° C. which corresponds to the melting process.

The definition of "polymorph" according to the FDA in its Guidance for Industry—ANDAs: Pharmaceutical Solid Polymorphism—July 2007: Polymorphic forms in the context of this guidance refer to crystalline and amorphous forms as well as solvate and hydrate forms, which are described below:

Crystalline forms have different arrangements and/or conformations of the molecules in the crystal lattice Amorphous forms, consists of disordered arrangements of molecules that do not posses a distinguishable crystal lattice Solvates are crystals forms containing either stoichiometric or nonstoichiometric amounts of a solvent. If the incorporated solvent is water, the solvate is commonly known as a hydrate.

Other drugs may have different solid phases (polymorph) of a trihydrated phase, but to date this is not the case for the zoledronic acid. The following phases have been identified and characterized: one solid phase for monohydrate, one solid phase for trihydrate and one or two anhydrous (with this last phase we still have some doubts). However, the different trihydrate solid phases that may exist, as well as the different solid phases of a monohydrate and/or all possible phases of the anhydride form are collectively referred to as a polymorph.

EXAMPLES

Merely for illustrative purposes, not limiting to the scope of this invention, the following preparation examples are included:

Example 1

Zoledronic Acid

Phosphorous trichloride (856 ml) is slowly added with stirring to a suspension of 1-imidazol-1-yl acetic acid (200 g) in methanesulfonic acid 98-99% (240 ml)

The temperature is increased until reaching 55° C., reflux is observed.

Once the phosphorous trichloride addition is finished, the addition of water (171 ml) is started, thus increasing the exothermy, which is evidenced through a larger volume of reflux.

During the reaction hydrogen chloride is released.

The mass in suspension slowly dissolves and the solution turns very viscous, thus making agitation difficult.

After 12 hours reaction at 55-70° C., water is slowly added (805 ml), in a period of 2-3 hours at a temperature between 8 and 25° C., with which a fluid solution is achieved.

It is then heated at 105-112° C. over 3 hours and the solution is filtered to eliminate impurities.

The resulting solution is partially neutralized at a temperature of 30-40° C. with a sodium hydroxide aqueous solution 50% (w/v) until obtaining a pH of 0.25±0.03.

It is then cooled down to 0-5° C., maintaining this temperature over at least 2 hours and the solid is filtered off.

The solid is washed by resuspension once in water (500 ml) and twice in methanol (500 ml each time).

The precipitate is dried in an oven at 50-60° C., thus obtaining the crude zoledronic acid with a potentiometric titre equal to or exceeding 98%.

It may also be used wet to prepare the trihydrate form.

The yield is 83%.

Example 2

Zoledronic Acid Trihydrate

The crude wet zoledronic acid (equivalent to 30 g dry product), obtained in Example 1, is suspended in water (900 ml).

The suspension is heated at reflux, thus obtaining a solution.

This hot solution is slowly added and stirring to a refrigerated container, containing water (50 ml).

The internal temperature is adjusted by means of the flow of refrigerant fluid and the volume of aggregate of the hot concentrated solution, in order to keep it between 15 and 25° C.

The addition requires around 3½ hours.

Once all the zoledronic acid solution is added, it is cooled down to 0-5° C. maintaining this temperature over 2-3 hours, the solid is filtered, washed with ice water (30 ml) and dried with air flow at 50-60° C.

The obtained product presents the following physico-chemical characteristics:

Diffraction by X-rays (powder method)

It presents peaks in at following values of 2θ 9.2; 10.4; 14.7; 16.4°±0.2°.

The diffractogram is the one shown in FIG. 1.

Assay (potentiometric): 99%

Humidity (Loss on drying): 16.6%

TGA (Thermogravimetric Analysis):

The obtained curve is shown in FIG. 2.

DSC (Differential Scanning Calorimetry)

The obtained curve is shown in FIG. 2.

Infrared Spectrum (KBr)

Absorption at 3578-3011; 1643.6; 1579.9; 1549.1; 1443.0; 1414.0; 1387.0; 1294.4; 1155.5; 966.5 cm$^{-1}$ Corresponds to FIG. 3.

Repeated experiments followed by characterization of the monohydrated, trihydrated and anhydrous forms demonstrate that the procedure according to the invention offers solids with less than 5% monohydrate and/or anhydride content.

Example 3

Zoledronic Acid Monohydrate

The crude wet zoledronic acid (equivalent to 190.3 g dry product), obtained according to Example I, is suspended in water (3050 ml).

The suspension is heated at reflux, with agitation.

Water is added up to a total volume of 3750 ml, by which a total dissolution is obtained.

The heating and the agitation is then interrupted, allowing it to slowly cool down to ambient temperature.

Once the internal temperature is around 70-80° C. the crystallization starts, and is substantially completed well before reaching 35° C.

Once the ambient temperature is reached, it is cooled down to 2-5° C., maintained at that temperature during 1½ hours, filtered and the solid is washed with ice water.

It is dried in an oven with air flow at 5° C.-60° C.

169.3 g (89%) colorless crystals are obtained.

The loss on drying (6.8%) confirms that this is a monohydrate.

This substance, by X-rays diffraction powder method, presents peaks at the following values of 2θ 12.1; 12.8; 15.7; 18.9; 21.7, 22.8; 27.8±0.2, coincident with those described for the form I (US 2005/0054616).

FIG. 1A shows its diffractogram of powder X-rays and FIG. 4A the arrangement of the atoms in the unit cell of the crystalline network for this form.

Example 4

Thermal Analysis—Zoledronic Acid Monohydrate vs. Trihydrate

Introduction

Polymorphs, as hydrates of an active pharmaceutical ingredient, may differ in key properties such as solubility, dissolution rate, stability, and particle habit. Hydrates represent different chemical entities as defined primarily by the stoichiometry of water to the active and in certain cases by different crystal structures. Depending upon the nature of the hydrate, the water content may or may not change over time with ambient humidity, temperature, or other processing and storage conditions. Accordingly, it is important to know, during the development of pharmaceuticals, if the water molecules are tightly coordinated and packed inside the crystal lattice. Depending on that, several problems could be generated. Many drugs are receiving regulatory approval for only a single crystal form or "polymorph".

In this Example, thermogravimetric analysis (TGA) is used as an analytical methodology to quantify the thermal stability parameters of solid chemicals. The data generated from these measurements is analyzed to obtain Arrhenius kinetic parameters such us activation energy (Ea) and preexponential factor. The activation energies of two different hydrates—zoledronic acid monohydrate and trihydrate—is obtained to analyze the dehydration reaction of these two forms to anhydrous form so that the their relative solid-state thermal stability can be ranked based on their activation energy values.

The results obtained indicate that zoledronic acid trihydrate has a solid-state kinetic thermal stability greater than monohydrate form.

Procedure

Thermogravimetric analysis (TGA) is a thermal analysis technique which measures the amount and rate of change on the weight of a material as a function of temperature or time in a controlled atmosphere. TGA measurements are used primarily to determinate the composition of materials and to predict their thermal stability up to elevate temperatures. However, with proper experimental procedures, additional information about the kinetics of decomposition and in-use lifetime predictions can be obtained.

TGA Kinetics Analysis method covers determination of the kinetic parameters, Arrhenius activation energy preexponential factor by thermogravimetry, based on the assumption that the decomposition to obeys first-order kinetics.

This program utilizes data gathered by running a sample at various heating rates. The program allows analysis of results from TGA data files to calculate the heating rate at each conversion percentage, and then generate plots and tables of kinetic analysis results. The program operates in accordance with the ASTM Standard E1641 (Standard Test Method for Decomposition Kinetics by Thermogravimetry).

Traditionally, isothermal and constant heating rate thermogravimetric analysis have been used to obtain kinetic information, with the constant heating rate method developed by Flynn & Wall being preferred because it requires less experimental time. The constant heating rate, or conventional TGA, approach is based on the Flynn & Wall method which requires three or more determinations at different linear heating rates, usually between 0.5 and 50° C./minute.

The approach assumes the basic Anhenius equation.

$$\left(\frac{d\alpha}{dt}\right) = Z\exp(-Ea/RT)(1-\alpha)^n$$

where:
a=Fraction of decomposition
t=Time (seconds)
Z=pre-exponential factor (1/seconds)
Ea=Activation energy (J/mole)
R=gas constant (8.3 14 J/mole K)
n=reaction order (dimension less)

Materials and Instrumentation

Materials: Zoledronic acid monohydrate BFI 10929 and trihydrate BFI 10781 was obtained from GADOR S.A. API Division, R&D lab. The samples were characterized by loss on drying and X-ray diffraction.

Analytical Methodology

X-ray Diffraction: X-ray powder diffraction was executed using a Philips equipment X'Pert model with the unit PW3710. Scans were performed over the range of 5°-40° 2θ, at a 0.02° step size for 2 s per step.

Thermal Analysis: Thermogravimetry analysis curves were generated using a TGA Q-500 V6.4 TA Instruments®. The analysis was performed with TGA Kinetics Analysis TA Instruments®; program Specialty Library V2. 1 Build 2.1.0.1.

Two to 5 mg samples were scanned at 5, 10 and 20° C./mm from 25 to 200° C. under dry nitrogen purge.

Results

Thermogravimetric Analysis Curves

Figure 5:
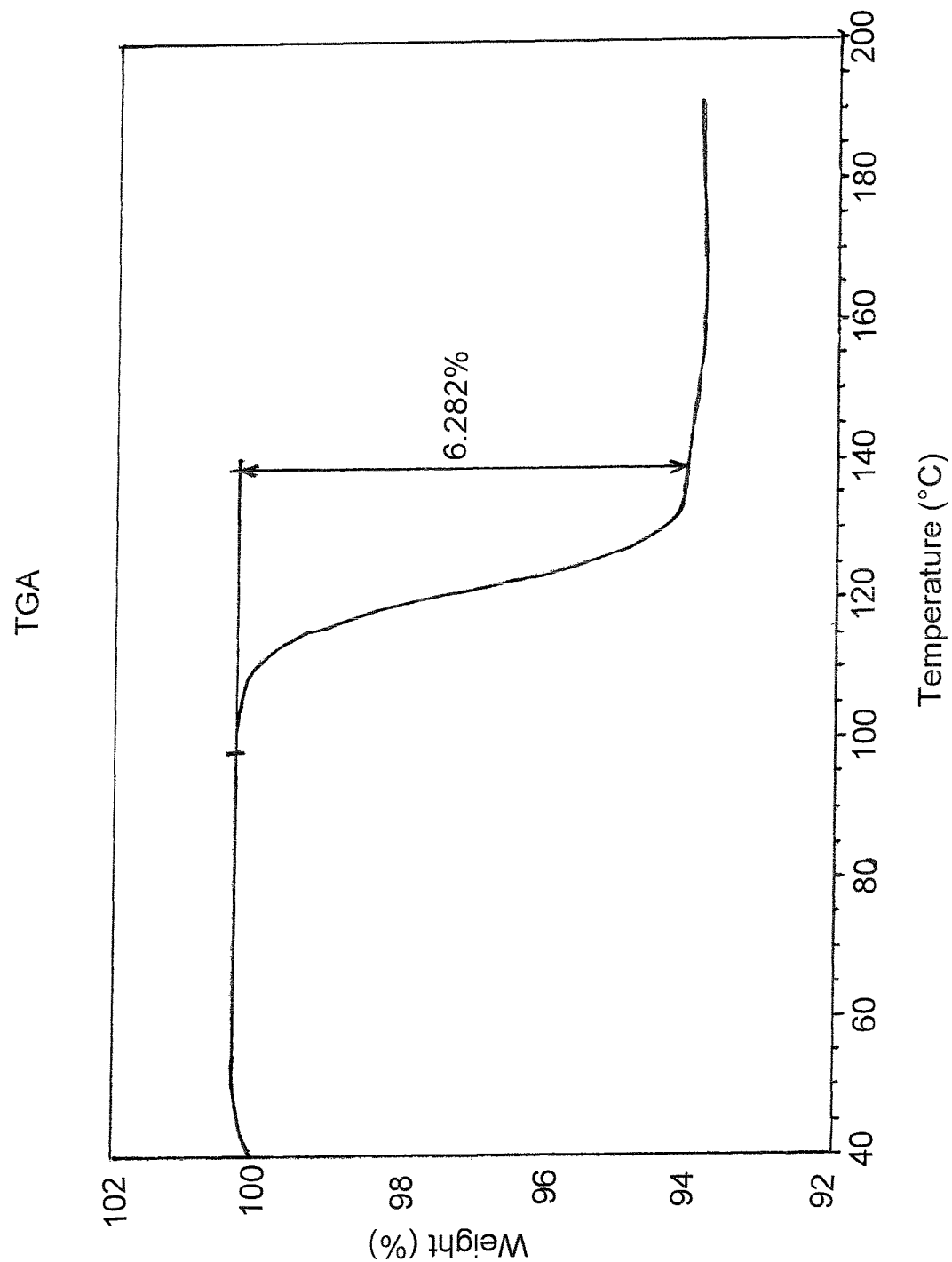
FIGS. 5a,b show representative thermogravimetric analysis curves obtained during thermogravimetric analysis.

Representative curves obtained (ramps at 10° C./mm) during the thermogravimetric analysis are shown in FIGS. 5a and 5b.

TGA Kinetics Analysis Plot

The heating rate versus F[p(x)] was graphed for different fraction of conversion (a) for the analyzed data files. Data points fit closely to the straight line, so the experimental data fits the mathematical model on which the determination is based.

Figure 7:
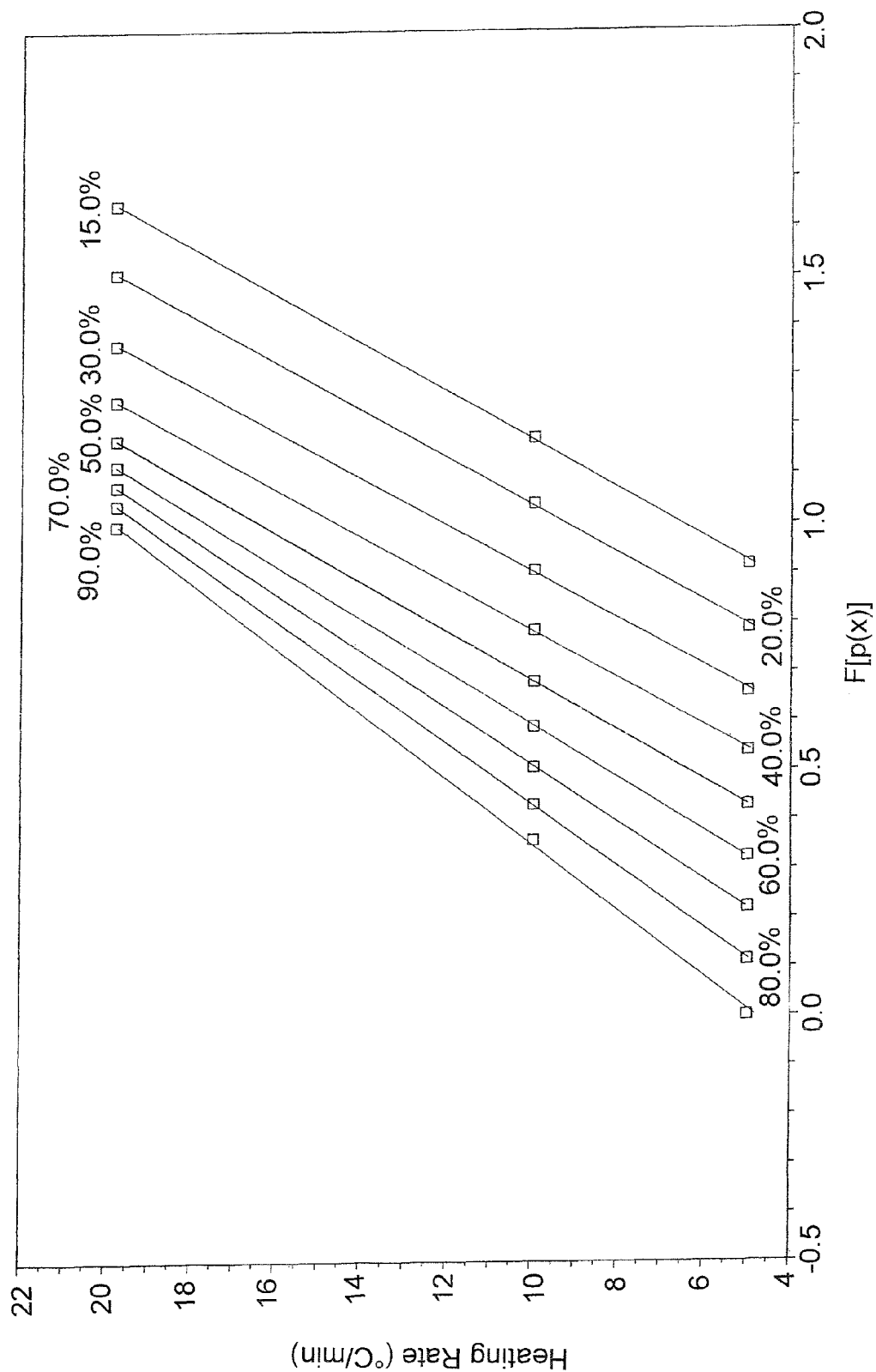
FIGS. 7 and 8 are TGA kinetics analysis plots, plotting heating rate versus $F[p(x)]$ for different fractions of conversion (a) for the analyzed data files.
Figure 8:
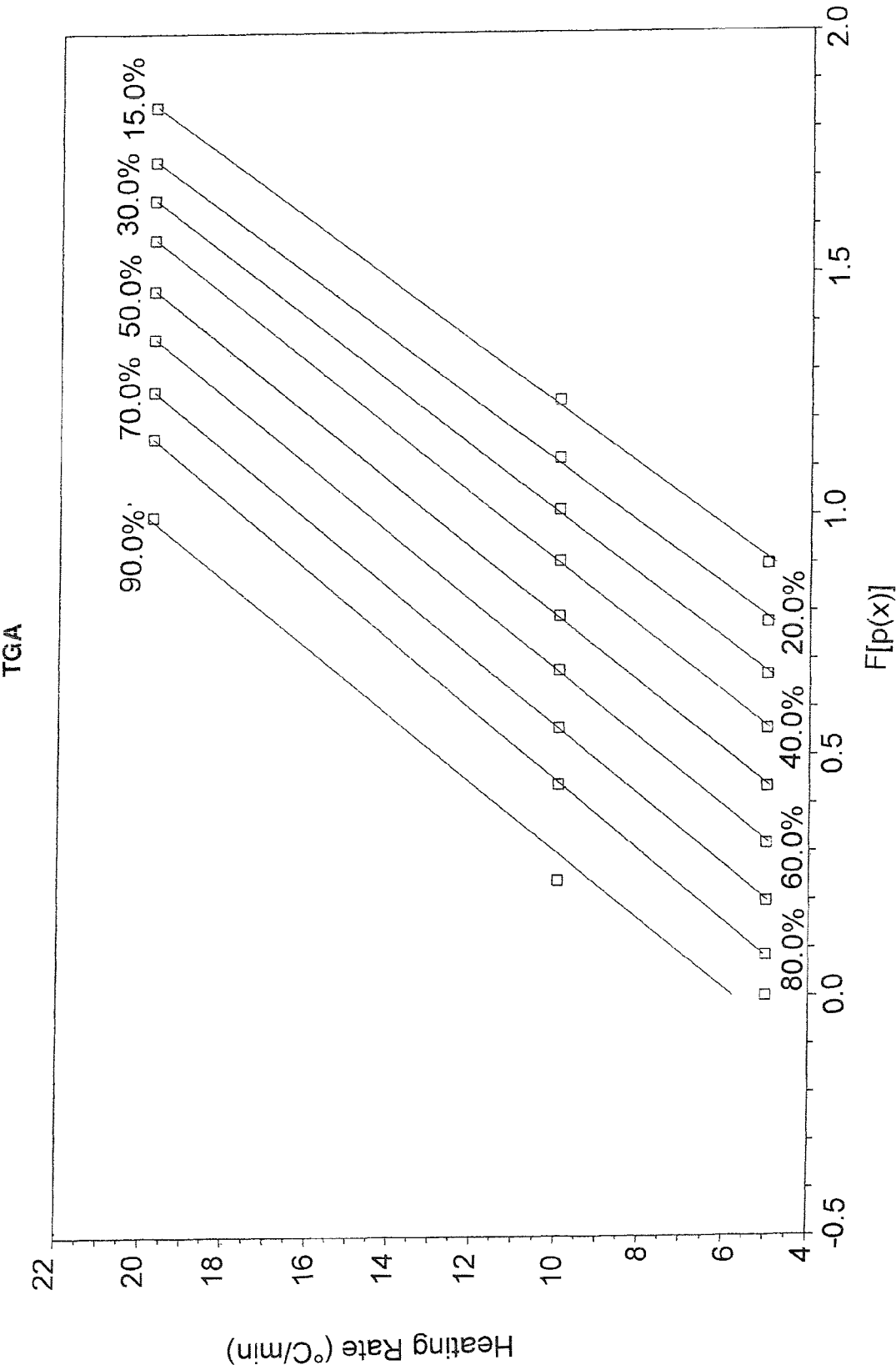

These results determine that kinetic reactions of dehydration for the solid forms of zoledronic acid monohydrate and trihydrate fit the mathematical model analyzed (see FIGS. 7 and 8).

From these analyses the kinetic parameter activation energy was calculated for each hydrate.

Figure 6:
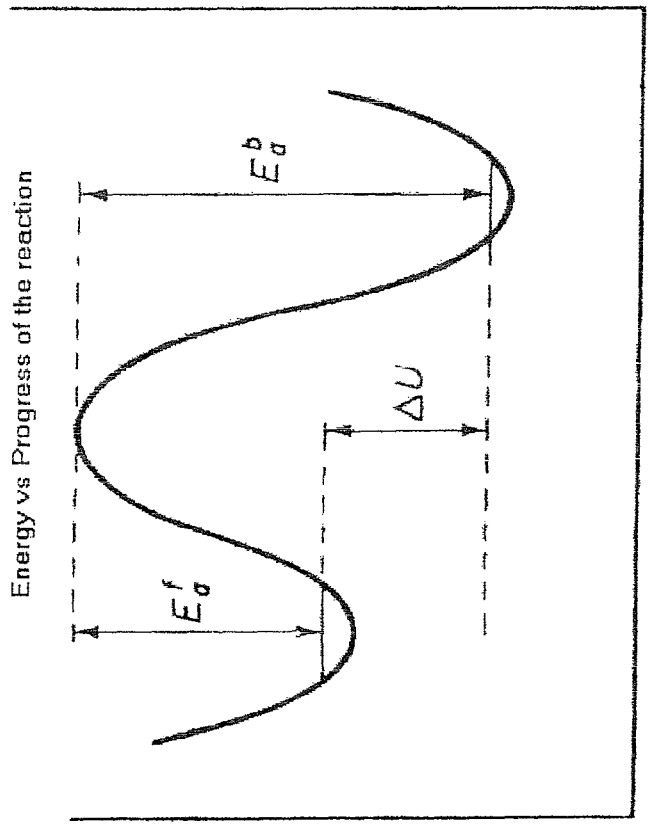
FIG. 6 illustrates the concept of activation energy Ea showed in a graph of reaction profile.

The concept of activation energy Ea is showed in the graph of reaction profile, see FIG. 6. The activation energy represents the amount of energy necessary to begin a chemical reaction and so convert the reagents to products.

In the case of the trihydrate, the activation energy parameter represents the amount of energy necessary for hydrate forms of Zoledronic acid to start the loss of water molecules. The higher the Ea value is, the more difficult the loss of water molecules become.

Kinetics Parameters

The obtained activation energy values from samples of Zoledronic acid monohydrate and trihydrate were different.

Zoledronic acid monohydrate had an Activation energy 152.0 kJ/mole at 50.0 percent of conversion level. Whereas that Zoledronic acid trihydrate had an Activation energy 79.9.0 kJ/mole at 50.0 percent of conversion level.

Conclusion: Constant heating thermogravimetric analysis (TGA) was used to evaluate the solid-state thermal stability of Zoledronic acid monohydrate and trihydrate. The obtained data for each sample at different heating rates were further processed by TGA Kinetics Analysis method to estimate the activation energy values. Based on the determined activation energy values, the relative kinetic-thermal stability of Zoledronic acid trihydrate is greater than Zoledronic acid monohydrate.

Example 5

Pharmaceutical Composition

In this example the product solution was composed of the following:

| Ingredient | Function | Weight/vial |
|---|---|---|
| Zoledronic acid, trihydrate | Active ingredient | 4.794 mg (Eq 4 mg zoledronic acid) |
| Sodium Chloride | Tonicity agent | 43.000 mg |
| Sodium Hydroxide | pH adjuster | 1.100 mg (or up to pH 6.0-6.5) |
| Water for injection | Vehicle | Qs To 5 ml |

Zoledronic acid was dissolved with water at room temperature. The rate of dissolution was further increased by the addition of sodium hydroxide which lead to the formation of a sodium salt (disodium salt in greater percentage) of zoledronic acid. Sodium chloride was selected as a tonicity agent and sodium hydroxide as a pH-adjusting agent.

During process development, the manufacturing steps and critical process parameters were be identified (for example: water temperature, mixing times/speed, choice of pre-filter if it was necessary with respect to filter rate; eventual drug removal during filtering, pre-filtration bioburden values, fill weight).

The compatibility of the bulk solution with the filters and tubing material was studied. The compatibility of the concentrate for solution for infusion with packaging materials (vials+stoppers) and with infusion media (5% glucose solution and 0.9% sodium chloride solution in plastic and glass devices) was be demonstrated by verifying the compliance with drug product specifications during stability studies. As part of the container/closure integrity test a microbiological challenge test with the primary packaging materials (upright and inverted position) was performed.

Description of the Manufacturing Process:
1. 19 kg of water for injection was loaded into a stainless steel container which has been previously weighed.
2. Temperature was checked: it should be below 30° C.
3. 90% of the total amount of sodium hydroxide was added and mechanical stirring was activated until dissolution was complete.
4. Zoledronic acid trihydrate was added and the solution is stirred until the API (active pharmaceutical ingredient) was completely dissolved.
5. Sodium chloride was added and dissolved.
6. In a separate stainless steel container, 200 g of water for injection was weighed, and the rest of the sodium hydroxide was dissolved with the aid of hand stirring.
7. The solution from step 6 was added to the bulk solution in a quantity sufficient to reach a target pH of 6.2 (range: 6.0-6.5), under constant mechanical stirring.
8. Water for injection was added to complete 20 L (determined by weight according theoretical density). The product was subjected to mechanical stirring for at least 5 minutes. pH and density were determined on a sample.
9. The solution was sterile-filtered. Chemical quality control and bacterial endotoxins were determined in a sample.
10. Sterile bulk solution was aseptically filled into sterilized (plastic) or depyrogenized (glass) vials. Fill volume (or its equivalent weight) was checked.
11. Filled vials were capped with sterilized stoppers and caps.
12. Terminal steam sterilization was carried out, according instructions of Ph Eur Conclusion: The crystalline trihydrate form of the zoledronic acid demonstrated good relative kinetic-thermal stability (providing a direct benefit for the active agent in bulk formulations, achieving a longer storage period in the warehouse, and a lesser chance for the solid active to undergo any changes during storage in the warehouse) and also API characteristics that improved stability and handling during formulation. Many other crystal hydrates, in contrast, tend to lose water and release it into the environment during the formulation process, increasing the possibility of drug degradation. These technical improvements do not affect the drug's bioavailability, since same is administered via injection.

Now that the invention has been described,
We claim:

1. A procedure for preparing crystalline zoledronic acid trihydrate, comprising:
   (a) dissolving zoledronic acid in a solvent at an elevated temperature to obtain a concentrate; and
   (b) progressively contacting the solution of step (a) with a lower temperature phase to crystallize zoledronic acid, such that substantially all crystallization occurs within the range of 5 to 35° C.

2. The procedure as in claim 1, further comprising:
   (c) further cooling the (suspension) of step (b), filtering the solid and washing the filtrated solid with water; and
   (d) drying the washed solid.

3. The procedure as in claim 1, wherein substantially all crystallization occurs within the range of 15 to 25° C.

4. The procedure as in claim 1, wherein said solvent is water.

5. The procedure as in claim 1, wherein said lower temperature phase is water.

6. The procedure as in claim 1, wherein said lower temperature phase is metal or glass.

7. The procedure as in claim 6, wherein said metal or glass are in the form of a tube.

8. The procedure as in claim 2, wherein an X-ray powder diffraction pattern of the product of step (d), at a K-alpha wavelength of 1.54060, presents peaks in angles of $2\theta$ at the following values: 9.2; 10.4; 10.8; 14.7; 16.4; 17.1; 18.4; 21.5; 21.8; 22.8; 25.0; 25.4; 27.8°±0.2°.

9. The procedure as in claim 8, wherein X-ray powder diffraction was executed with scans performed over the range of 5°-40°2θ, at a 0.02° step size for 2 s per step.

10. The procedure as in claim 1, wherein thermogravimetry demonstrates that the zoledronic acid trihydrate has an activation energy of 179.9 kJ/mole at 50.0 percent of conversion level.

11. The procedure as in claim 1, wherein a study by means of X rays of a single crystal of zoledronic acid trihydrate shows that the distribution of its atoms in the crystalline network corresponds to the special group P-i, characterized by the following cell parameters (A): a:6.874; b: 9.450; c:10.825; $\alpha$ (alpha):65.140; $\beta$ (beta):76.83 0; $\gamma$ (gamma): 81.390.

12. The procedure as in claim 1, wherein the crystalline trihydrate product, upon exposure in an environment with 75 to 96% relative humidity at 30-40° C. during 24 hours, does not absorb water and maintains its X-rays powder diffractogram and its thermal profile (TGA and DSC) unchanged.

13. The procedure as in claim 1, wherein thermal analysis (TGA and DSC) of the crystalline trihydrate product shows an endotherm between 68-128° C. associated with a loss of mass of around 16-17%, which corresponds to a trihydrate, and a melting endotherm followed by decomposition at around 211-215° C.

14. A procedure to prepare a crystalline form of trihydrated zoledronic acid, comprising the following steps:
   a. reacting 1-imidazol-1-yl acetic acid with phosphorous trichloride and water, using methanesulphonic acid as a solvent, in an absence of phosphorous acid;
   b. hydrolyzing, by adding water and heating, the intermediate substances generated in the reaction;
   c. precipitating the crude acid of the reaction means, through partial neutralization and cooling;
   d. dissolving the crude zoledronic acid in solvent at elevated temperature to form a concentrated solution;
   e. introducing the concentrated solution into refrigerated water, so that crystallization occurs at a temperature below the elevated temperature;
   f. once the crystallization is completed, further cooling down the product of step (e), filtering the precipitate and washing it with water; and
   g. drying the product of step (f).

15. The procedure according to claim 14, wherein the molar ratio in step a. of phosphorous trichloride: 1-imidazol-1-yl acetic acid is from 3:1 to 8:1.

16. The procedure according to claim 14, wherein the molar ratio in step a. of phosphorous trichloride: water is from 0.8:1 to 1.2:1.

17. The procedure according to claim 14, wherein the hydrolysis in step b. is conducted at a temperature between 80 and 125° C., for a time of at least half an hour.

18. The procedure according to claim 14, wherein the neutralization in step c. is conducted by means of an aqueous solution of hydroxides or carbonates of alkaline metals.

19. The procedure according to claim 14, wherein in the partial neutralization, the solution is adjusted to a pH from 0 to 0.9.

20. The procedure according to claim 14, wherein in the partial neutralization, the solution is adjusted to a pH from 0 to 0.4.

21. The procedure according to claim 14, wherein the concentration of the zoledronic acid in the hot solution of the step d. is from 1 to 3.5% (w/v).

22. The procedure according to claim 14, wherein the dissolution temperature of the step d. is comprised from 50 to 105° C., 17.

23. The procedure according to claim 22, wherein the dissolution temperature is within the range from 80 to 100° C.

24. The procedure according to claim 14, wherein the crystallization temperature of the step e. is from 5 to 35° C., inclusive.

25. The procedure according to claim 14, wherein the crystallization temperature is from 15 to 25° C.

26. The procedure according to claim 14, wherein the drying of step g. is at atmospheric pressure and at a temperature from 20 to 80° C.

27. The procedure according to claim 26, wherein the drying is made at the atmospheric pressure and at a temperature from 30 to 60° C.

* * * * *